(12) United States Patent  
Gusterson

(10) Patent No.: US 7,400,709 B2  
(45) Date of Patent: Jul. 15, 2008

(54) X-RAY INSPECTION SYSTEM

(75) Inventor: Steve Gusterson, Kettering (GB)

(73) Assignee: Mettler-Toledo Safeline X-Ray Limited, Royston (GB)

( * ) Notice: Subject to any disclaimer, the term of this patent is extended or adjusted under 35 U.S.C. 154(b) by 8 days.

(21) Appl. No.: 11/536,254

(22) Filed: Sep. 28, 2006

(65) Prior Publication Data

US 2007/0223656 A1     Sep. 27, 2007

(30) Foreign Application Priority Data

Sep. 30, 2005   (GB)   ................... 0519925.2
Sep. 30, 2005   (GB)   ................... 0519926.0

(51) Int. Cl.
*G21K 5/10*     (2006.01)
(52) U.S. Cl. .................. 378/146; 378/57; 378/98.8
(58) Field of Classification Search ................ 378/98.8, 378/146, 19, 57, 58;  250/370.08, 370.09
See application file for complete search history.

(56) References Cited

U.S. PATENT DOCUMENTS 4,736,401 A *   4/1988   Donges et al.   ............. 378/146

2004/0251415 A1   12/2004   Verbinski et al.

FOREIGN PATENT DOCUMENTS

EP   0198276 A1   10/1986
JP   2004257884 A   9/2004

* cited by examiner

*Primary Examiner*—Courtney Thomas
(74) *Attorney, Agent, or Firm*—Carstens & Cahoon LLP

(57) ABSTRACT

An x-ray inspection system (198) arranged to inspect at least one object and comprising: a source of radiation (200) a detector (216), in use, capable of detecting the radiation passing through an irradiation zone (214) and generating a periodic output of data therefrom; processing circuitry arranged to process the output generated by the detector (216); a speed determination means (228) arranged, in use, to determine and output to the processing circuitry the speed at which an object passes the detector (216); wherein the processing circuitry is arranged to vary the period of the output of the detector (216) according to the output from the speed determination means (228).

13 Claims, 4 Drawing Sheets

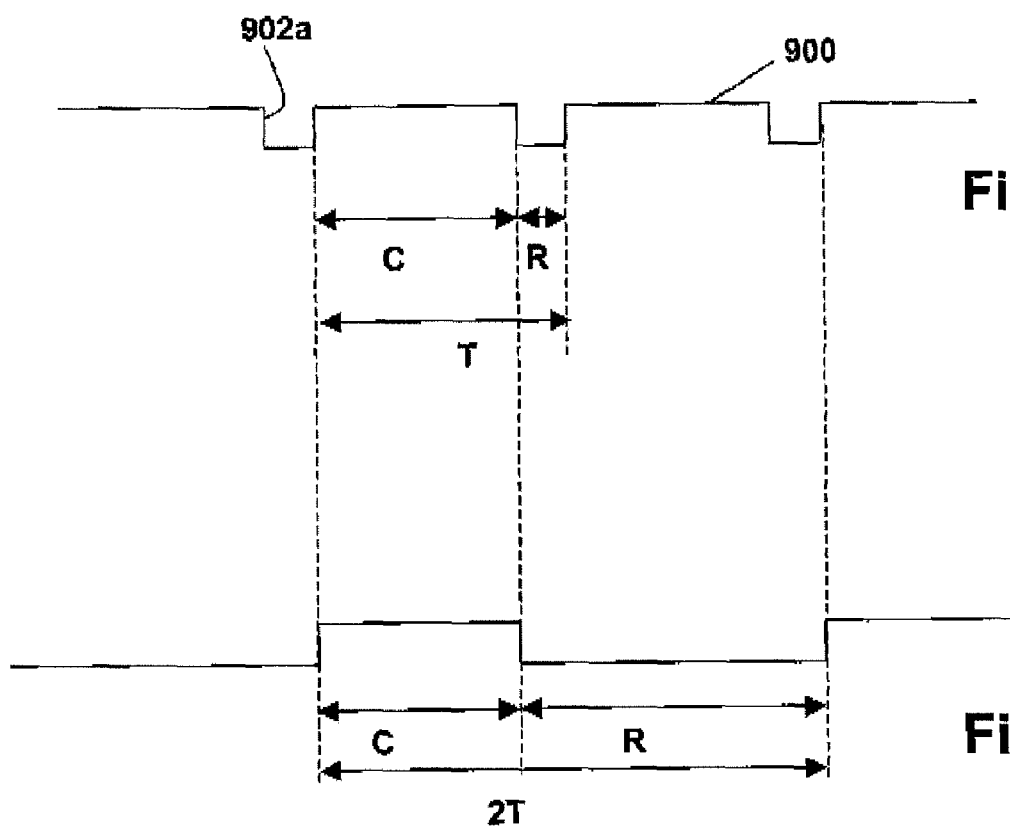

X-RAY INSPECTION SYSTEM

CROSS-REFERENCE TO RELATED AP0PLICATION

This application claims priority based on GB application number GB 0519926.0 filed Sep. 30, 2005, and GB application number GB 0519925.2 filed Sep. 30, 2005.

This invention relates to an x-ray inspection system and related methods of inspecting articles using x-rays.

There is an on-going need to inspect articles, whether this is the inspection of baggage in an airport, or other transport related situation, or in the output of a production process. For example, it is common in the food industry to inspect the actual content of the food in order to determine that the food content is as desired and does contain any foreign bodies such as stones, bone fragments, metal from the machines used in the production of the food, or the like.

A typical x-ray inspection apparatus comprises a conveyor arranged to carry objects to be inspected through the apparatus. Within the apparatus there is an x-ray source with a collimator associated therewith arranged to produce a narrow irradiation zone extending across the conveyor. Beneath the conveyor there is provided a detector arranged to detect x-rays which have passed through an object, on the conveyor, passing through the irradiation zone.

The detector generally comprises a linear array of photo-diodes, extending across the conveyor, adjacent the irradiation zone, The photo-diodes are generally provided in a series of modules, each of which contains a plurality of photo diodes. A phosphorescent strip is mounted above the photo-diodes within a module and x-rays which are incident upon the phosphorescent strip cause light to be emitted therefrom. The intensity of the light emitted from the phosphorescent strip is proportional to the amount of x-rays that are incident upon it and the light output is detected by the photo-diodes.

Thus, the output from the photo-diodes can be used to give an indication of the amount of x-rays which are reaching the phosphorescent strip through the irradiation zone. The amount of x-rays reaching the phosphorescent strip will be dependent upon the nature of the object which is passing through the irradiation zone; denser materials such as bone, metal, stone and the like will absorb more x-rays that material such as meat, or other foodstuffs. Likewise, the absence of material, such as due to a void, will absorb less x-rays than meat or other foodstuff, Therefore, the amount of x-ray reaching the phosphorescent strip can be used to determine whether there is foreign matter in the product, or indeed whether there is an absence of matter.

The output of the photo-diodes is commonly converted into a video display and/or processed in order to determine whether the object passing the irradiation zone meets predetermined criteria.

Generally, the detector (e.g. the photo-diodes) is maintained in a fixed orientation and the object/product to be scanned is moved past the detector using a conveyor. Some applications in which such an x-ray inspection system might be used vary the speed of the conveyor. These applications include the monitoring of pharmaceutical or foodstuff packaging lines to ensure that the packaging is correctly filled with pharmaceutical/foodstuff; the monitoring of fluids or solids within a pipeline (e.g. soup and minced meat respectively); and other similar applications.

Processing circuitry provided to process the output of the detector is generally calibrated to the speed at which the object to be scanned passes the detector. Therefore, if the speed of the conveyor is altered, the speed at which the object passes the detector alters, and the calibration of the processing circuitry becomes wrong.

Many x-ray inspection systems function to automatically reject objects which do not meet predetermined criteria. Therefore, if the calibration is inaccurate, some objects may be rejected unnecessarily, or perhaps worse, some objects which should be rejected may not be. Thus respectively, objects could be wasted, or objects which are sub-standard may be allowed to proceed.

According to a first aspect of the invention there is provided an x-ray inspection system arranged to inspect at least one object and comprising:

a source of radiation;

a detector, in use, capable of detecting the radiation passing through an irradiation zone and generating a periodic output of data therefrom;

processing circuitry arranged to process the output generated by the detector;

a speed determination means arranged, in use, to determine and output to the processing circuitry the speed at which an object passes the detector; wherein the processing circuitry is arranged to vary the period of the output of the detector according to the output from the speed determination means.

According to a second aspect of the invention there is provided a method of monitoring a product comprising; measuring the speed at which the product passes through an irradiation zone in which x-rays generated by an x-ray source are incident; detecting the amount of x-rays that pass through the product using a detector adjacent the irradiation zone and having a periodic output; wherein the method comprises adjusting the period of the output according to the speed at which the object passes through the irradiation zone.

According to a third aspect of the invention there is provided a computer readable medium containing instructions which when read by a processing circuitry cause that processing circuitry to provide the system of the first aspect of the invention.

According to a fourth aspect of the invention there is provided a computer readable medium containing instructions which when read be a processing circuitry cause that processing circuitry to perform the method of the second or third aspects of the invention.

The computer readable medium in any of the above aspects of the invention may be any of the following: a floppy disk; a CDROM; a DVD (including +R/+RW, −R/−RW, RAM); a hard disk; a memory (including memory sticks and the like); a tape; a transmitted signal (including an Internet download, an ftp transfer and the like); a wire; or the like.

There now follows by way of example only a detailed description of the present invention with reference to the accompanying drawings in which FIG. 1 shows an arrangement of photo-diodes within an x-ray inspection system;

FIG. 4 shows a timing diagram for circuitry used to drive the photo-detector array shown in the earlier Figures.

Figure 1:
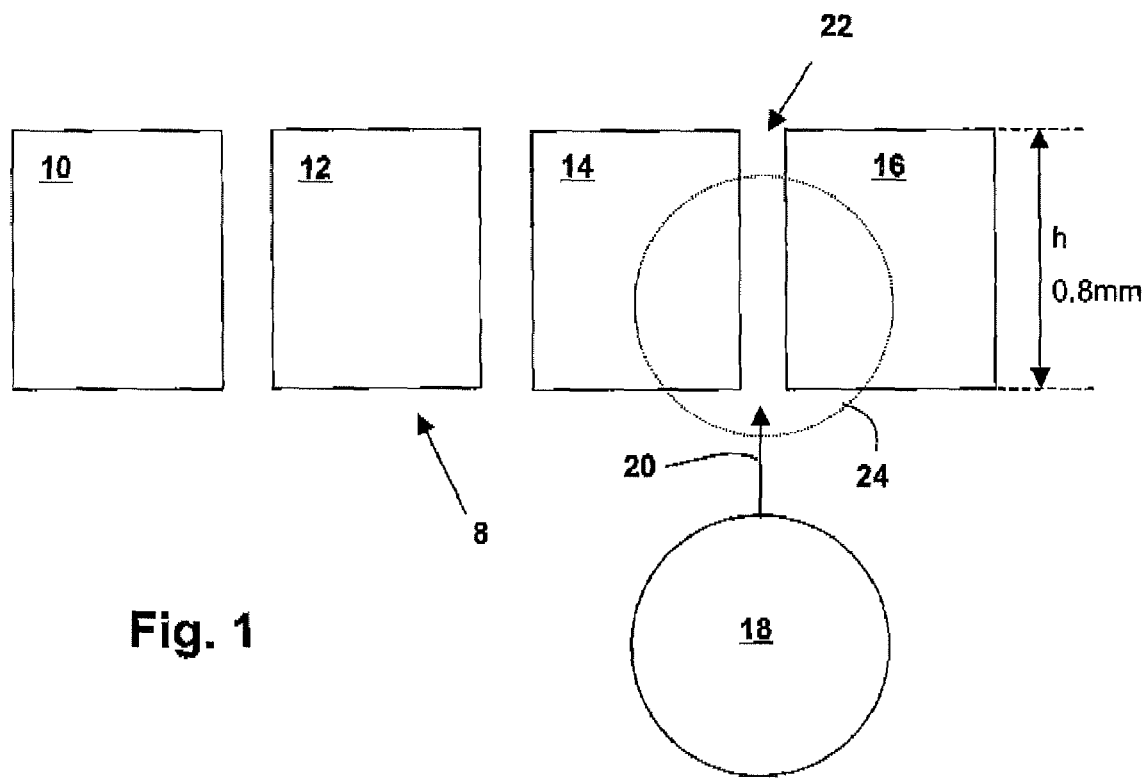

FIG. 1 is used to discuss an arrangement of a prior art x-ray inspection system which typically comprises a photo-diode array made up of discrete diodes arranged in a single row. A photo-diode array typically comprises 64 diodes and four of the diodes 10-16 in the array 8 are shown in FIG. 1. It will be readily appreciated by a person skilled in the art that the photo-diode array may comprise any number of photo-diodes wherein the number used will be determined by the application.

Figure 2:
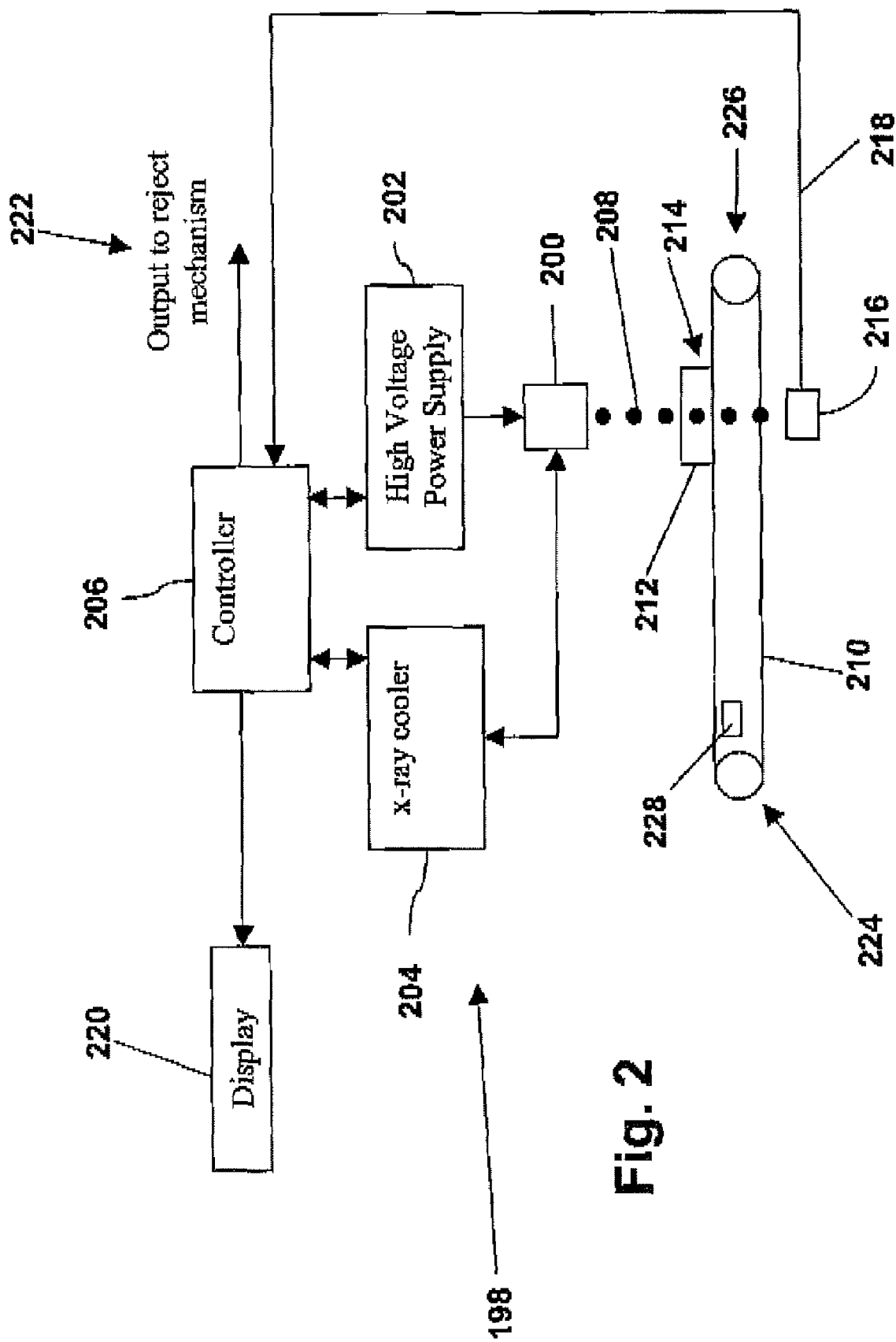
FIG. 2 shows a typical arrangement of the components of an x-ray inspection system.

FIG. 2 shows a general arrangement of an x-ray inspection system 198. This Figure is intended to put embodiments of the invention into context but may also be applicable to prior art systems. The system is intended to inspect objects to ensure that the inspected object is suitable and/or safe for its intended purpose. If the object were a foodstuff, or a pharmaceutical then the inspection may be to determine whether there are foreign bodies or voids therein, or an absence of product within the packaging. If the object is an item of baggage then the inspection may be to determine whether there banned goods in the baggage; for example to inspect baggage before an airline flight.

The system comprises an x-ray source 200, providing a source of radiation, which is supplied from a high voltage power supply 202. The x-ray source is cooled by a cooler 204 to ensure that its temperature is maintained within an operating range. The power supply 202 and the cooler 204 are controlled by the processing circuitry within a controller 206 which is discussed hereinafter.

Figure 3:
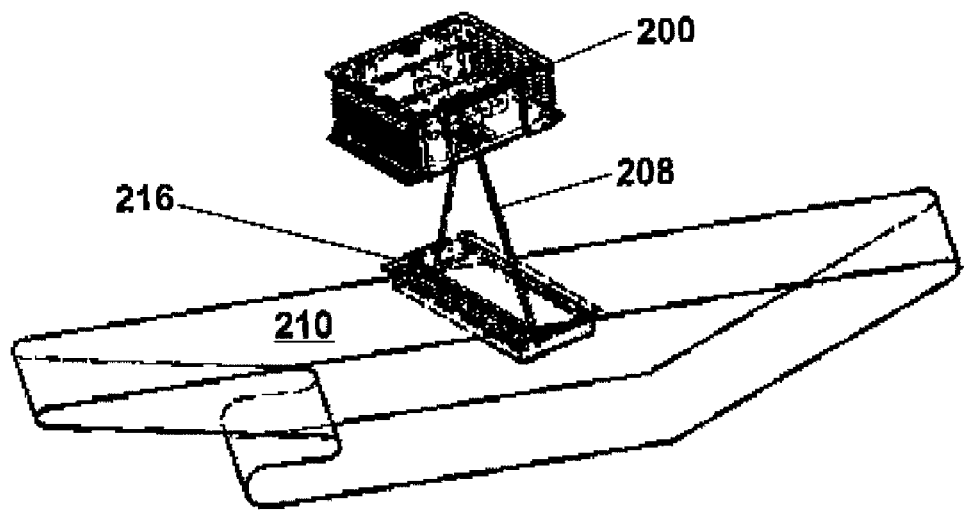
FIG. 3 shows an 3 dimensional view of the arrangement of a photo diode array

The x-rays produced by the x-ray source 200 are collimated, in a known manner, to provide a thin beam of x-rays of generally a fan shape 208 (which shape can best be seen in FIG. 3) and typically having a width of roughly 1 mm. In FIG. 2 the fan shape is viewed from one side and is represented by a row of dots.

A conveyor 210, having an upstream end 224 from which objects flow and a downstream end 226 to which objects flow, is provided and arranged to move an object 212 to be inspected through an irradiation zone 214 situated in a region below the x-ray source 200 and above an x-ray detector 216, which comprises a plurality of detector elements, each arranged to generate a periodic output. The conveyor 216 is shown in FIG. 2 as being a belt conveyor but could be any other suitable form of mechanism arranged to transfer objects 212 through the irradiation zone 214, such a Bandolier or web conveyor mechanisms or the like, It will be appreciated that if the direction of travel of the conveyor 210 is reversed then the upstream end 224 will become the downstream end 226 and visa versa.

Some conveyor mechanisms may use packaging of the object as the conveyor (such as in packaging of pharmaceuticals). Other conveyor mechanisms may provide conduits for fluids such as soups, or the like. In such an embodiment the fluid is the object to be inspected. However, it is likely to still be desirable to inspect the content of objects carried by such transport mechanisms to ensure that the product is suitable and/or safe to be released.

The detector 216 is arranged to output data indicative of the amount of x-rays incident thereupon. The x-rays emitted from the source 200 generally pass through the object 212 when it is in the irradiation zone 214, but are attenuated by the object 212 according to its composition, and are then detected by the x-ray detector 216. The amount of x-rays received at a point along the detector (i.e. into or out of the page as viewed in FIG. 2) give an indication of the composition of the object 212 at that point along the detector 216 at that point in time.

As the object 212 (which may be a fluid, or packaging that should contain an object) is moved through the irradiation zone 214 by the conveyor 210 a two dimensional image of the object can be constructed from the data output from the detector 216. That is, the data output from the detector can be taken at predetermined intervals (typically roughly 1 ms) and stitched together to form an image after suitable processing In this embodiment, an output 218 from the detector 216 is processed by the processing circuitry of the controller 206 which generates a video display which is output to a display 220.

In some embodiments, the controller 206 may also perform other processing on the data output from the detector 216, for example to determine whether the product being scanned should be rejected by making an output on an 'Output reject mechanism' 222. In such embodiments if the controller 206 determines that the object being scanned is below a predetermined standard (may be because it contains a foreign body above a predetermined size, it contains a void, a portion of the packaging is unfilled or the like) then it can cause a rejection mechanism to remove the object from the conveyor 210. Such rejection mechanisms are well known and will not be described further.

In some embodiments, the display 220 may be omitted and the machine may perform automatic inspection of an object passing through the irradiation zone 214, During automatic inspection, if the controller 206 determines that a product falls outside acceptable criteria then the output to the reject mechanism 222 can be utilized to remove the product from the conveyor 210.

The processing circuitry of the controller 206 typically comprises a processor such as an Intel™ Pentium™, AMD™ Athlon™, IBM™ PowerPC™, or other such processor. However, in other embodiments the processing circuitry may also comprise dedicated electronics as provided by one or more Application Specific Integrated Circuits (or the like).

The processor is arranged to run code held in a memory accessible by the processor. The memory may or may not be provided within the system 198 and may be accessible over a network connection to the system 198. Further, it is likely that the memory comprises both a volatile portion (e.g. RAM) and a non-volatile portion (e.g. ROM, EPROM, a hard drive, or the like).

The display 220 is typically a Liquid Crystal Display (LCD) but could be any other type of display such as a Cathode Ray Tube (CRT) display, a Light Emitting Polymer (LEP) display or the like.

In FIG. 1, four detector elements 10, 12, 14, 16, are shown. A detector element would generally be a photo diode, The detector elements are provided in modules which are arranged to provide the detector. Typically a module would contain 64 photo diodes but this need not be the case and 32 and 128 diode modules are also known. It is possible that a module could contain any number of photo diodes.

In one embodiment there are fourteen modules in the detector 216. However, other embodiments may have different numbers of detector modules which make up the detector 216. Indeed, the detector may not comprise modules. The number of modules is generally sufficient to provide detection across the width of the conveyor 210 which is used to transport objects 212 through the irradiation zone 214. Current embodiments generally have anywhere between roughly 4 and 20 modules, However, some embodiments have as many as 72 modules and it is conceivable that more detector or less modules could be employed. Therefore, in a system employing 72 modules, each having 64 detector elements therein, would employ 4608 detector elements (e.g. photo diodes).

The image displayed on the display 220 is pixelated in nature as will be the corresponding image which is held in the memory of the processing circuitry of the controller 206 due to the digital nature of the electronics generally used.

In an embodiment, when an image is processed, any object 212 on the conveyor 210 is assumed to have moved a predetermined distance in between samples taken of the outputs from the detector 216. Therefore, a fixed conveyor is speed is generally assumed. It is convenient that this speed is calculated to be length of the diodes in the direction of travel of the conveyor 210 multiplied by the scan rate:

$$\text{velocity} = \text{height } (h) \times \text{scan rate}. \quad (1)$$

Using the example of FIG. 1, the diodes have a height (h) in the direction of conveyor travel of 0.8 mm and the system has a scan rate of 1000 scan/s (i.e. a 1 ms period). Therefore, in the system of FIG. 1 an object would appear correctly on a display thereof (and within the memory) if the conveyor 210 were to be travelling at 0.8 mm×1000 scan/s—i.e. 800 mm a second. Halving the scan speed to 500 scans/s would reduce the speed of the conveyor to which the system is matched (i.e. require no correction) to 400 mm/sec.

If such a fixed speed is assumed and the conveyor 210 travels at greater than this speed then the objects will appear, on the display 220, shorter than they should. Likewise, if the conveyor 210 travels at a lower speed then objects 212 will appear to be longer than they should. This can be problematic for processing performed by the controller 206 on the data output from the detector 216. For example, embodiments of the system may be arranged to process data output from the detector 216 in order to obtain a volume of an object (for example, a bar of chocolate, etc.), If the length of the bar were to vary because of the conveyor speed change then the volume would appear to fluctuate leading to the potential rejection of objects with an acceptable volume and/or the retention of objects with an unacceptable volume. Further, embodiments of the system may be used to determine whether foodstuffs (for example chocolates), pharmaceuticals, or the like, fill each cell of the packaging. A varying conveyor speed may lead to the controller 206 determining that a foodstuff, pharmaceutical, etc. is in a location which it does not actually occupy; i.e. it has been shifted.

There now follows a discussion in relation to FIG. 4 which embodiments of the present invention may employ in order to correct processing of the data output from the detector 216 to the speed of the conveyor 210. Each of the detector elements is generally a photo-diode with which there is an associated scintillating layer of material (generally a strip of phosphorous). This is well known in the art.

Further, the photo-diodes are generally reversed biased so that they function as a charged coupled device: as x-rays hit the scintillating layer light is generated; the generated light causes charge to be stored in the photo-diode; the magnitude of the charge on any one diode is read at a predetermined interval (as such the output from the detector is periodic); and after the level of charge is read the diode is reset so that the accumulated charge is removed therefrom, The level of charge, on any one photo-diode, read in this manner gives an indication of the amount of x-rays that were incident upon the scintillating material in a region above that photo-diode. Thus, photo-diodes in the detector 216 are reset at a regular intervals which are generally kept constant in order that the charge measured from the photo-diode is measured over a constant time period.

FIG. 4a shows a suitable waveform 900 for resetting the photo-diodes in the detector. The waveform has a period T which comprises a low, reset, pulse 902 of period R which is used to reset the photo-diode and a high pulse of period C which allows charge to be accumulated on the diode, the period C may be thought of as a measurement pulse. The output from the detector is generally read at an end region of this measurement pulse before the detector is reset. It will be seen that the period T is substantially constant for the waveform 900 such that the edges of the reset pulse occur at a predetermined time.

In order to accommodate a varying conveyor speed the skilled person may think that it would simply be a matter of altering the period T of the waveform 900 such that an object 212 on the conveyor moves a predetermined distance in between each reset pulse 902. However, there are complex calibration issues involved and if the period T is altered the system needs to be recalibrated in order to maintain the output of the detector 216 constant. This is not a practical solution particularly in applications of the system in which the speed of the conveyor 210 continuously varies. Such applications include the packaging of pharmaceuticals into blister packs comprising a plurality of blisters; the filling of continuously banded pouches of powder, or the like, monitoring fluids (such as soup) or pumped solids (such a minced meats) in a pipeline; and the like.

In embodiments of the invention the processing performed on the data output from the detector 216 is compensated according to a method and apparatus which is described in relation to FIGS. 4a and 4b.

It is assumed that the apparatus is largely as described in relation to FIG. 2 although the skilled person will appreciate how the teachings in relation to FIGS. 4a and 4b could be applied to apparatus of a different arrangement. In order to set up the method a determination is made of the maximum speed at which it will be desired to run the conveyor 210 and the controller 206 is configured to process data generated by the detector 216 appropriately. Part of this configuration is to set the periods T, C and R; the total period (T), the period in which charge is allowed to accumulate (C) and the reset period (R). In the method being described T and R vary whilst C remains constant. The period C is set during initial calibration of the system 198 and is calculated to give the required exposure of x-rays to the detector during the measurement period (i.e. period C). Once period, C has been set the periods T and R can be varied without affecting calibration of the system 198 since the detector will still be receiving the required exposure in each period of the output of the detector (e.g. period T).

In an embodiment of the invention the period C is kept constant and the period R is varied as described below; therefore, the period T (i.e. the period of the output of the detector) also varies. Thus, in this embodiment the duration of the reset pulse applied to the detector is controlled. For example, the period C may typically be set to a period of roughly 1 ms although other values such as roughly any of the following may also be suitable: 100 µs, 500 µs, 1.5 ms, 5 ms, 10 ms or any value in between these values.

As discussed above, in the period C of the waveform 900, charge accumulates on the photo-diodes within the detector 216. Calibration of the outputs of the individual photodiodes, the gain of the detector as a whole, and the like, requires that the period C remain constant. However, if the speed of the conveyor were to change then the speed of scanning of the data output from the detector needs to alter in order that the speed of the conveyor matches the scan speed according to the equation (1) above.

Therefore, if the speed of the conveyor were to halve (e.g. from 800 mm/s to 400 mm/s) then the scan rate would also have to halve; that is the period T would have to double. In order to achieve this, the period R is increased in order to give the desired period T, keeping C constant (it is noted that R+C=T). Such an occurrence is shown in FIG. 4b.

For example, assuming the 0.8 mm height h of FIG. 1, a conveyor velocity of 800 mm/s which would result in a scan speed of 1 m/s (i.e. 1000 scans/s) we could assume that C is 990 μs and R is 10 μs. Thus, the sum of R and C gives a period of 1 ms which is the required scan rate. If the speed of the conveyor were to slow to 400 mm/s the scan rate would halve (i.e. T becomes 2 ms) but C remains constant and therefore R becomes 1010 μs. Thus, controller 206 can accommodate a varying conveyor speed without the need to recalibrate the system. FIG. 4b shows an example in which the period T has been doubled when compared to FIG. 4a but in which the period C remains constant.

Because when the system 198 is initially set up the maximum speed of the conveyor is determined, and the system set appropriately then the period T will never need to be decreased below this initial setting. Thus, as the conveyor 210 slows the period T is increased in proportion to the slowing of the conveyor 210. If the speed of the conveyor 210 subsequently increases then period T can be again be reduced. In order to achieve this the system 198 comprises a speed detector 228. The speed determination means 228 may be any suitable device such as an optical encoder, ferro magnetic coil, capacitive sensors, a switch (such as a micro switch, a reed switch or the like) or other device.

Thus, in use the system 198 using a method as described with reference to FIG. 4 may be used for an application in which the speed of the conveyor 210 is periodically varied.

In one particular example, the x-ray inspection system 198 is used to examine blister packs wherein each of the blisters in the package should have been filled with a capsule by the packaging process. If the controller 206 determines, by, processing the data output from the detector 210 that one or more blisters of the package do not contain a capsule then an output is made on the 'Output reject mechanism' 222 to reject that blister pack. The peak velocity of the conveyor 210 in this system is 60 m/s but the average velocity is 40 m/s. Thus, it is likely that a blister pack will be accelerating as it passes through the irradiation zone 214. The method of varying the period C described in relation to FIG. 4 allows the processing circuitry in the controller 206 to correctly process the data output from the detector 216 to identify whether each blister of the blister pack is full and avoid any of the problems discussed above.

The invention claimed is:

1. An x-ray inspection system arranged to inspect at least one object and comprising:
   a source of radiation;
   a detector, which in use, is configured to detect the radiation passing through an irradiation zone and generating a periodic output of data therefrom, wherein the period of the output comprises a duration of a measurement pulse and a duration of a reset pulse;
   wherein the detection is arranged such that radiation is detected when a measurement pulse occurs;
   processing circuitry arranged to process the output generated by the detector;
   a speed determiner arranged to determine and output to the processing circuitry the speed at which an object passes the detector; wherein the processing circuitry is arranged to vary the period of the output of the detector according to the output from the speed determiner whilst maintaining the duration of the measurement pulse at a substantially constant period.

2. A system according to claim 1 in which the processing circuitry is arranged to vary the period of the output by controlling the duration of the reset pulse applied to the detector.

3. A system according to claim 1 in which the processing circuitry is arranged to measure the output of the detector at an end region of the measurement pulse.

4. A system according to claim 1 in which the detector comprises a plurality of photo-diodes.

5. A machine readable medium containing instructions which cause a processing circuitry to function as the system of claim 1 when run thereby.

6. An x-ray inspection system arranged to inspect at least one object and comprising:
   a source of radiation;
   a detector, which in use, is configured to detect the radiation passing through an irradiation zone and generating a periodic output of data therefrom, wherein the period of the output comprises a duration of a measurement pulse and a duration of a reset pulse;
   processing circuitry arranged to process the output generated by the detector;
   a speed determiner arranged, in use, to determine and output to the processing circuitry the speed at which an object passes the detector;
   wherein the processing circuitry is arranged to vary the period of the output of the detector according to the output from the speed determiner, and is further arranged to vary the period of the output by controlling the duration of the reset pulse applied to the detector.

7. A system according to claim 6 in which the processing circuitry is arranged to maintain the duration of the measurement pulse, during which radiation is detected, at a substantially constant period.

8. A machine readable medium containing instructions which cause a processing circuitry to function as the system of claim 6 when run thereby.

9. A method of monitoring a product comprising: measuring the speed at which the product passes through an irradiation zone in which x-rays generated by an x-ray source are incident; detecting the amount of x-rays that pass through the product using a detector adjacent the irradiation zone and having a periodic output comprising a duration of a measurement pulse and a duration of a reset pulse, radiation being detected when the measurement pulse occurs;
   wherein the method comprises adjusting the period of the output according to the speed at which the object passes through the irradiation zone, whilst maintaining the duration of the measurement pulse at a substantially constant period.

10. A method according to claim 9 which controls the duration of a reset pulse applied to the detector in order to adjust the period of the output.

11. A method according to claim 9 which reads the output from the detector at an end region of the measurement pulse.

12. A method according to claim 9 which sets the duration of the measurement pulse according to the maximum speed at which the object will pass through the irradiation zone.

13. A computer readable medium containing instructions which when read by a processing circuitry cause that processing circuitry to perform the method of claim 9.

* * * * *